United States Patent [19]
Calandruccio et al.

[11] Patent Number: 5,743,918
[45] Date of Patent: Apr. 28, 1998

[54] INSTRUMENTATION FOR AND METHOD FOR IMPLANTING A SPHERICAL PROSTHESIS

[75] Inventors: James H. Calandruccio; Mark T. Jobe, both of Memphis, Tenn.

[73] Assignee: Wright Medical Technology, Inc., Arlington, Tenn.

[21] Appl. No.: 645,178

[22] Filed: May 13, 1996

[51] Int. Cl.$^6$ ................................................ A61B 17/56
[52] U.S. Cl. ........................ 623/21; 623/18; 623/66; 606/102; 128/898
[58] Field of Search ........................ 623/11, 16, 17, 623/18, 20, 21, 22, 23, 57, 61; 128/898; 606/60, 61, 62, 63, 79–85, 90, 99, 100, 102, 105, 174, 176–180, 183, 205–207, 211; D24/140

[56] References Cited

U.S. PATENT DOCUMENTS

| | | | |
|---|---|---|---|
| 4,106,128 | 8/1978 | Greenwald et al. | 128/92 |
| 4,501,269 | 2/1985 | Bagby | 128/92 |
| 4,566,466 | 1/1986 | Ripple et al. | 128/781 |
| 4,834,757 | 5/1989 | Brantigan | 623/17 |
| 4,936,848 | 6/1990 | Bagby | 623/17 |
| 5,122,130 | 6/1992 | Keller | 606/61 |
| 5,192,327 | 3/1993 | Brantigan | 623/17 |
| 5,326,364 | 7/1994 | Clift, Jr. et al. | 623/21 |

OTHER PUBLICATIONS

Metcalfe, J. W.: "Vitallium Sphere Prosthesis for Nonunion of the Navicular Bone"; *Journal of the International College of Surgeons*, 22: 459–462, 1954.

Legge, R. F.: "Vitallium Prosthesis in the Treatment of Fracture of the Carpal Navicular"; *The Western Journal of Surgery, Obstetrics & Gynecology*, 59: 468–471, Sep. 1951.

*Primary Examiner*—John G. Weiss
*Assistant Examiner*—Francis K. Cuddihy
*Attorney, Agent, or Firm*—Walker, McKenzie & Walker, P.C.

[57] ABSTRACT

A method of and instrumentation for implanting a spherical prosthesis in a joint between a first bone and a second bone. The method includes the steps of exposing a joint between a first bone and a second bone; forming a semispherical cavity in the proximal surface of the first bone; forming a semispherical cavity in the distal surface of the second bone; and inserting a spherical prosthesis into the semispherical cavities in the proximal surface of the first bone and in the distal surface of the second bone.

The instrumentation includes cutting instrument including a cutting instrument head having the shape of a segment of a sphere with at least one truncated end or side, and a shaft attached to the cutting instrument head for allowing the cutting instrument head to be inserted between the proximal end of a first bone and the distal end of a second bone, and to be then at least partially rotated about a rotational axis generally transverse to an axis or plane extending through the center of the segment of a sphere substantially perpendicular to the plane of the surface of the truncated end or side thereof.

The instrumentation also includes a trial instrument with a trial instrument head having the shape of a segment of a sphere for being inserted into the semispherical cavities in the proximal end of the first bone and the distal end of the second bone.

5 Claims, 5 Drawing Sheets

FIG. 23

INSTRUMENTATION FOR AND METHOD FOR IMPLANTING A SPHERICAL PROSTHESIS

BACKGROUND OF THE INVENTION

1. Field of the Invention

The present invention relates in general to instrumentation for and methods of implanting a spherical prosthesis in a joint between a first bone and a second bone, and more specifically to instrumentation for and a method of implanting a spherical prosthesis in the carpometacarpal joint of a patient's thumb.

2. Information Disclosure Statement

Various prostheses and methods have heretofore been developed for the replacement of damaged bones, skeletal articular surfaces and joints, including the bones of the human wrist and hand. For example, Metcalfe, J. W.: "Vitallium Sphere Prosthesis for Nonunion of the Navicular Bone"; *Journal of the International College of Surgeons*, 22: 459–462, 1954, and Legge, R. F.: "Vitallium Prosthesis in the Treatment of Fracture of the Carpal Navicular"; *The Western Journal of Surgery, Obstetrics & Gynecology*, 59:468–471, September, 1951, disclose vitallium sphere prostheses for the complete replacement of a fractured scaphoid (navicular) bone.

The articular surfaces between the trapezium and the first, or thumb, metacarpal in a person's hand will sometimes degenerate due to conditions such as osteoarthritis or trauma, resulting in severe pain during thumb circumduction, etc. Clift et al., U.S. Pat. No. 5,326,364, issued Jul. 5, 1994, discloses a trapezial implant for replacing the distal surface of a trapezium. The method disclosed by Clift et al. includes exposing the carpometacarpal joint of the patient's thumb through a transverse or curved longitudinal incision; then resecting the distal end or saddle of the trapezium with an osteotome or power sagittal saw to create a flat distal surface; and then attaching a trapezial implant to the flat distal surface of the prepared trapezium by forcing a pair of pointed posts extending from the back side of the trapezial implant into the flat distal surface of the prepared trapezium.

Nothing in the known prior art discloses or suggests the present invention. More specifically, nothing in the known prior art discloses or suggests a method including the steps of exposing a joint between a first bone and a second bone; forming a semispherical cavity (e.g., a cavity substantially equal to an outer ⅓ of a sphere) in the proximal surface of the first bone; forming a semispherical cavity (e.g., a cavity substantially equal to an outer ⅓ of a sphere) in the distal surface of the second bone; and inserting a spherical prosthesis into the semispherical cavities in the proximal surface of the first bone and in the distal surface of the second bone. Likewise, nothing in the known prior art discloses or suggests a cutting instrument including a cutting instrument head having the shape of a segment of a sphere with at least one truncated end or side, and a shaft attached to the cutting instrument head for allowing the cutting instrument head to be inserted between the proximal end of a first bone and the distal end of a second bone, and to be then at least partially rotated about a rotational axis generally transverse to an axis or plane extending through the center of the segment of a sphere substantially perpendicular to the plane of the surface of the truncated end or side thereof; or a trial instrument including a trial instrument head having the shape of a segment of a sphere with a truncated end, and a shaft attached to the trial instrument head for allowing the trial instrument head to be inserted into semispherical cavities in the proximal end of a first bone and the distal end of a second bone, and to be then rotated about a rotational axis generally transverse to an axis extending through the center of the segment of a sphere substantially perpendicular to the plane of the surface of the truncated end or side thereof.

SUMMARY OF THE INVENTION

The present invention provides instrumentation and a method for implanting a spherical prosthesis in a joint between a first bone and a second bone.

The method of the present invention comprises, in general, the steps of exposing a joint between a first bone and a second bone; forming a semispherical cavity in the proximal surface of the first bone; forming a semispherical cavity in the distal surface of the second bone; and inserting a spherical prosthesis into the semispherical cavities in the proximal surface of the first bone and in the distal surface of the second bone. Such a method preferably produces a cavity in the proximal surface of the first bone that is equal to ⅓ of the spherical prosthesis and produces a cavity in the distal surface of the second bone that is equal to ⅓ of the spherical prosthesis, so that when the spherical prosthesis is implanted, ⅓ thereof will be surrounded by bone in the first bone, ⅓ thereof will be surrounded by bone in the second bone, and the central ⅓ thereof will be free of any support. The spherical prosthesis is not fixed, but is free to rotate in all directions as the joint moves.

A cutting instrument of the present invention comprises, in general, a cutting instrument head having the shape of a segment of a sphere with at least one truncated end or side, and a shaft attached to the cutting instrument head for allowing the cutting instrument head to be inserted between the proximal end of a first bone and the distal end of a second bone, and to be then at least partially rotated about a rotational axis generally transverse to an axis or plane extending through the center of the segment of a sphere substantially perpendicular to the plane of the surface of a truncated end or side thereof. The present invention may include a series or set of such cutting instruments having a graduated sequence of different size cutting instrument heads.

A trial instrument of the present invention comprises, in general, a trial instrument head having the shape of a segment of a sphere with at least one truncated end or side, and a shaft attached to the trial instrument head for allowing the trial instrument head to be inserted into semispherical cavities in the proximal end of a first bone and the distal end of a second bone, and to be then rotated about a rotational axis generally transverse to an axis extending through the center of the central segment of a sphere substantially perpendicular to the plane of the surface of a truncated end or side thereof. The present invention may include a series or set of such trial instruments having a graduated sequence of different size trial instrument heads.

BRIEF DESCRIPTION OF THE DRAWINGS

3

FIG. 12 is a somewhat diagrammatic, sectional view of the first metacarpal and the trapezium of a left hand, similar

4 to FIG. 11 but diagrammatically showing the spherical prosthesis thereof fully implanted in the semispherical cavities in the proximal surface of the first metacarpal and the distal surface of the trapezium.

DESCRIPTION OF THE PREFERRED EMBODIMENTS

Figure 1:
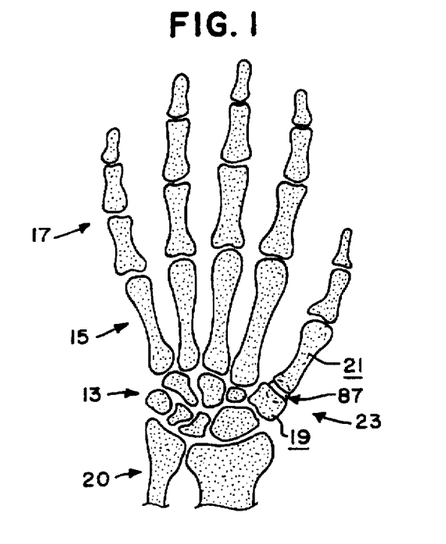
FIG. 1 is a dorsal view of the bones of a left hand, showing a spherical prosthesis implanted in the superior or proximal surface of the base of the first or thumb metacarpal and the inferior or distal surface of the trapezium.

As shown diagrammatically in FIG. 1, the skeleton of a human hand includes the bones of the carpus or wrist 13, the bones of the metacarpus or palm 15, and the bones of the phalanges or digits 17. The carpus 13 includes eight bones arranged in a proximal carpal row including a scaphoid (or navicular), a lunate, a triquetrum, and a pisiform, and a distal carpal row including a trapezium 19, a trapezoid, a capitate, and a hamate. The proximal surfaces of the proximal carpal row articulate generally with the distal surfaces of the radius and ulna of the forearm 20. The distal surfaces of the distal carpal row articulate generally with the base or proximal ends of the metacarpal bones to form the carpometacarpal joints. The metacarpus 15 includes a first or thumb metacarpal 21, a second metacarpal, a third metacarpal, a fourth metacarpal, and a fifth metacarpal. The phalanges 17 include three generally long bones for each finger and two for the thumb. The present invention is especially designed for implanting a spherical prosthesis (e.g., the spherical prosthesis 87) in the carpometacarpal joint 23 of a human hand between the first or thumb metacarpal 21 and the trapezium 19 (see, in general, FIG. 1).

In the preferred technique for implantation of a thumb carpometacarpal joint spherical prosthesis, after sterile preparation of the anesthetized upper extremity, the hand, forearm, and arm are exsanguinated and a tourniquet applied and inflated to 100 millimeter over systolic blood pressure. A 3.0 centimeter skin incision is centered about the thumb carpometacarpal joint 23. The incision may be curved and is oriented either dorsal or volar radial. Blunt dissection through the subcutaneous tissues should spare terminal sensory branches in this region and allow the retinaculum over the abductor pollicis longus and extensor pollicis brevis tendons to be clearly visualized.

The abductor pollicis longus and extensor pollicis brevis tendons are retracted and sharp dissection is utilized to form a proximally based capsular flap on the trapezium 19 incorporating a portion of the dorsoradial ligament. The flap is approximately 3 to 4 millimeters wide at its base. Retractors are placed into the joint 23 and the soft tissues separated to clearly view the surfaces of the trapezium 19 and thumb metacarpal 21. The joint 23 is debrided with a curet, removing loose bodies and osteophytes especially about the volar and ulnar margin of the joint.

Figure 2:
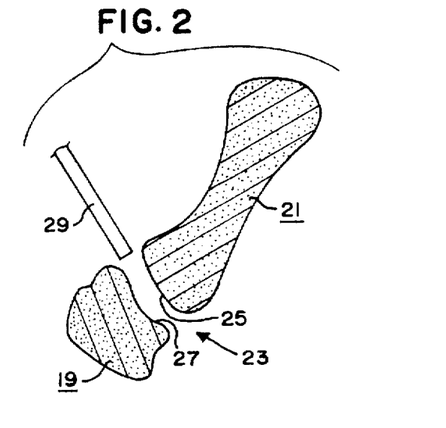
FIG. 2 is a somewhat diagrammatic, sectional view of the first metacarpal and the trapezium of a left hand, showing a feeler gauge being used to measure the gap between the proximal surface of the first metacarpal and the distal surface of the trapezium.

The distance between the proximal surface 25 of the thumb metacarpal 21 and the distal surface 27 of the trapezium 19 is then measured. This step of measuring the distance between the proximal surface 25 of the thumb metacarpal 21 and the distal surface 27 of the trapezium 19 preferably includes using an accurate measuring instrument or sizer such as a typical, medical grade feeler gauge 29 (see FIG. 2) to accurately determine the width of the gap between the proximal surface 25 of the thumb metacarpal 21 and the distal surface 27 of the trapezium 19 in a manner as will now be apparent to those skilled in the art.

Figure 3:
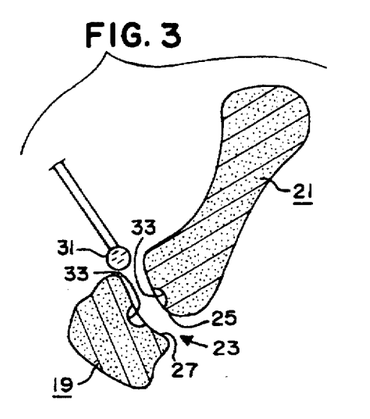
FIG. 3 is a somewhat diagrammatic, sectional view of the first metacarpal and the trapezium of a left hand, similar to FIG. 2 but showing a relatively small (e.g., 3 millimeters in diameter) rotary burr being inserted into the gap between the proximal surface of the first metacarpal and the distal surface of the trapezium to form a pilot hole in the proximal surface of the first metacarpal and in the distal surface of the trapezium.

A small cutting tool 31, such as a standard 3 millimeter rotary burr (see FIG. 3), may be then used to form (e.g., cut or grind) pilot holes 33 in the proximal surface 25 of the thumb metacarpal 21 and the distal surface 27 of the trapezium 19 by merely inserting the head of the cutting tool 31 into the gap between the proximal surface 25 of the thumb metacarpal 21 and the distal surface 27 of the trapezium 19 and cutting a small depression or hole 33 into the center of the proximal surface 25 of the thumb metacarpal 21 and the distal surface 27 of the trapezium 19. Such cutting tools are well known to those skilled in the art and may, for example, consist of a typical high speed bone drill such as disclosed by Shea et al, U.S. Pat. No. RE. 29,736, reissued Aug. 22, 1978.

At least one and preferably a series, set or group of custom cutting instruments, or burrs, are provided to form (e.g., cut or grind) semispherical cavities (e.g., cavities that are each substantially equal to an outer ⅓ of a sphere) in the proximal surface 25 of the thumb metacarpal 21 and the distal surface 27 of the trapezium 19, and, thereby, enlarge any pilot hole 33 that may have been previously formed in the proximal surface 25 of the thumb metacarpal 21 and the distal surface 27 of the trapezium 19. The size of the final semispherical cavities to be formed or cut in the proximal surface 25 of the thumb metacarpal 21 and the distal surface 27 of the trapezium 19 will vary between each individual patent and the group of cutting tools provided may start at a size to cut or form a semispherical cavity based on a spherical diameter of 3 millimeters or so, and increase in size by 0.5 millimeter until a final or largest cutting tool is provided at a size to cut or form a semispherical cavity based on a spherical diameter of 12 millimeters or so, thereby allowing the semispherical cavities to be formed in stages, starting at, e.g., 3 millimeters or so and increasing in size by 0.5 millimeter each step until the final size is achieved.

The specific size of the final semispherical cavities to be thus formed in the proximal surface 25 of the thumb metacarpal 21 and in the distal surface 27 of the trapezium 19 is preferably based on the measured gap between the proximal surface 25 of the thumb metacarpal 21 and the distal surface 27 of the trapezium 19. More specifically, the final semispherical cavities thus formed are preferably based on a spherical diameter equal to three times the width of the measured gap between the proximal surface 25 of the thumb metacarpal 21 and in the distal surface 27 of the trapezium 19.

A first embodiment of the cutting instrument of the present invention is shown in FIGS. 4–7 and 13–17, and is especially designed to fully rotate. This first embodiment preferably includes a series or set of similar cutting instruments having a graduated sequence of sizes to cut different size semispherical cavities.

Figure 4:
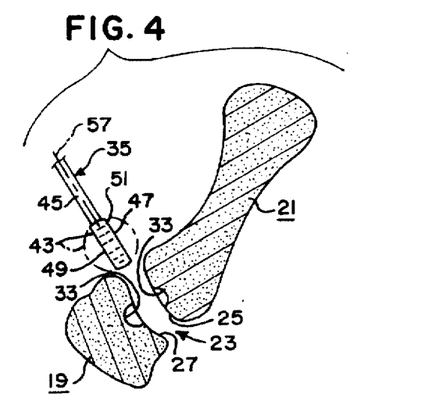
FIG. 4 is a somewhat diagrammatic, sectional view of the first metacarpal and the trapezium of a left hand, similar to FIG. 3 but showing a cutting instrument being inserted into the gap between the proximal surface of the first metacarpal and the distal surface of the trapezium to cut semispherical cavities (e.g., cavities that are each substantially equal to an outer ⅓ of a sphere) in the proximal surface of the first metacarpal and in the distal surface of the trapezium.
Figure 5:
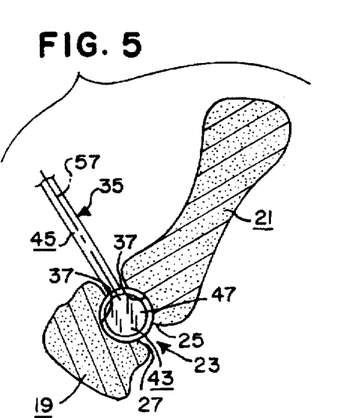
FIG. 5 is a somewhat diagrammatic, sectional view of the first metacarpal and the trapezium of a left hand, similar to FIG. 4 but showing the cutting instrument thereof fully inserted between the proximal surface of the first metacarpal and in the distal surface of the trapezium, and rotated 90° relative to the position shown in FIG. 4.
Figure 6:
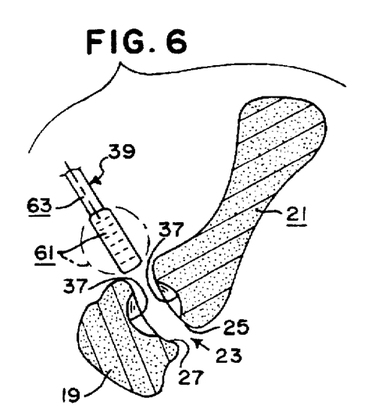
FIG. 6 is a somewhat diagrammatic, sectional view of the first metacarpal and the trapezium of a left hand, similar to FIG. 4 but showing an incrementally larger cutting instrument being inserted into the gap between the proximal surface of the first metacarpal and the distal surface of the trapezium to cut incrementally larger semispherical cavities in the proximal surface of the first metacarpal and in the distal surface of the trapezium.
Figure 7:
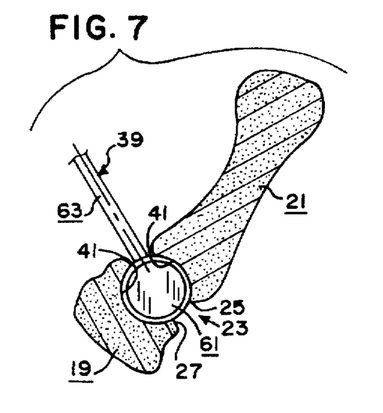
FIG. 7 is a somewhat diagrammatic, sectional view of the first metacarpal and the trapezium of a left hand, similar to FIG. 6 but showing the second cutting instrument fully inserted between the proximal surface of the first metacarpal and in the distal surface of the trapezium, and rotated 90° relative to the position shown in FIG. 6.
Figure 17:
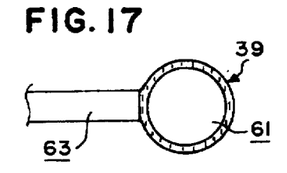
FIG. 17 is a top plan view of an incrementally larger cutting instrument of the instrumentation of the present invention.
Figure 18:
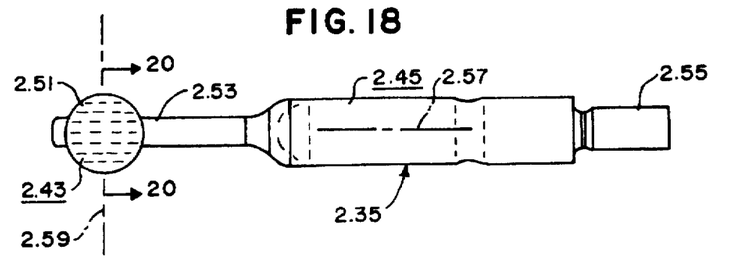
FIG. 18 is a top plan view of a second embodiment of the a cutting instrument of the instrumentation of the present invention.

Thus, this first embodiment preferably includes a cutting instrument 35 as shown in FIGS. 4, 5 and 13–16 (hereinafter referred to as the "first" cutting instrument 35) for cutting semispherical cavities 37 as shown in FIGS. 5 and 6 (hereinafter referred to as the "first" semispherical cavities 37) in the proximal surface 25 of the thumb metacarpal 21 and the distal surface 27 of the trapezium 19, and an incrementally larger cutting instrument 39 as shown in FIGS. 6, 7 and 17 (hereinafter referred to as the "second" cutting instrument 39) for enlarging the first semispherical cavities 37 by cutting incrementally larger semispherical cavities 41 as shown in FIGS. 7 and 9–12 (hereinafter referred to as the "second" semispherical cavities 41) in the proximal surface 25 of the thumb metacarpal 21 and the distal surface 27 of the trapezium 19, etc.

The first cutting instrument 35 is shown in detail in FIGS. 13–16 and includes, in general, a cutting instrument head 43 and an elongated shaft 45 attached to the cutting instrument head 43 for allowing the cutting instrument head 43 to be rotated. The cutting instrument head 43 preferably has the shape of a central segment of a sphere with a first truncated end 47, a second truncated end 49, and a semispherical cutting edge or face surface 51 extending between the first and second truncated ends 47, 49. The shaft 45 has a first end 53 attached or joined to the cutting instrument head 43 and a second end 55 adapted to be coupled to a typical oscillating or rotary drill, handpiece or the like as will now be apparent to those skilled in the art. The shaft 45 thus allows the cutting instrument head 43 to be rotated about a rotational axis 57 that is coextensive with the longitudinal axis of the shaft 45 and that is generally transverse to an axis or plane 59 extending through the center of the cutting instrument head 43 (i.e. through the central segment of the sphere) between (and preferably perpendicular to the planar face of) the truncated ends 47, 49 thereof (see FIGS. 14 and 15). While the specific size of the cutting instrument head 43 may vary to cut different size semispherical cavities as will now be apparent to those skilled, for purposes of this disclosure, the cutting instrument head 43 will be considered to be sized to cut or form a semispherical cavity based on a spherical diameter of, for example, 8.5 millimeters. Using such a cutting instrument causes the semispherical cavities 37 to be formed in the proximal surface 25 of the thumb metacarpal 21 and the distal surface 27 of the trapezium 19 at the same time, ensuring that the cavities 37 will align with each other. The thickness of the cutting instrument head 43 (i.e., the distance between the first end 47 and the second end 49) is preferably no greater than, and may be less than, the width of the gap between the proximal surface 25 of the thumb metacarpal 21 and the distal surface 27 of the trapezium 19 to allow the cutting instrument head 43 to easy slide between the proximal surface 25 of the thumb metacarpal 21 and the distal surface 27 of the trapezium 19 when turned or held sideways relative to the joint 23 as illustrated in FIG. 4. The cross sectional size or width of at least the first end 53 of the shaft 45 adjacent the cutting instrument head 43 is preferably less than the width of the gap between the proximal surface 25 of the thumb metacarpal 21 and the distal surface 27 of the trapezium 19 to allow that portion of the shaft 45 to easily fit and rotate between the proximal surface 25 of the thumb metacarpal 21 and the distal surface 27 of the trapezium 19.

The second cutting instrument 39 shown in FIGS. 6, 7 and 17 is preferably substantially similar of the first cutting instrument 35, including a cutting instrument head 61 and an elongated shaft 63 attached to the cutting instrument head 61 for allowing the cutting instrument head 61 to be rotated. However, the cutting instrument head 61 of the second cutting instrument 39 preferably has the shape of a central segment of a sphere that is 0.5 millimeters in diameter larger than that of the cutting instrument head 43 of the first cutting instrument 35. Thus, based on the above example of the cutting instrument 43 being sized to cut or form a semispherical cavity based on a spherical diameter of, for example, 8.5 millimeters, the cutting instrument head 61 will be considered to be sized to cut or form a semispherical cavity based on a spherical diameter of, for example, 9.0 millimeters.

The size of the "final" matched pair of partial hemispherical impressions or semispherical cavities formed with the first embodiment of cutting instruments is preferably based on a spherical diameter equal to three times the width of the measured gap between the proximal surface 25 of the thumb metacarpal 21 and in the distal surface 27 of the trapezium 19. To form the matched pair of partial hemispherical impressions or semispherical cavities having a desired size based on the measured distance or gap between the proximal surface 25 of the thumb metacarpal 21 and in the distal surface 27 of the trapezium 19 in the proximal surface 25 of the thumb metacarpal 21 and in the distal surface 27 of the trapezium 19, using the first embodiment of the cutting instrument of the present invention, the measured distance or gap provides the size of the "final" cutting instrument to use. Thus, for example, if the measured distance or gap is 3.0 millimeters, the "final" cutting instrument will be the second cutting instrument 39 which, as hereinabove described, is sized to cut or form semispherical cavities 41 based on a spherical diameter of 9.0 millimeters (i.e., three times the measured distance or gap). However, the "initial" cutting instrument used may be sized to cut or form semispherical cavities based on a spherical diameter of 3.0 millimeters, followed by a series of incrementally larger cutting instruments sized to cut or form semispherical cavities based on a spherical diameter of 0.5 millimeters larger each step than the preceding cutting instrument, until the "final" cutting instrument (e.g., the second cutting instrument 39) is used to thereby cut or form semispherical cavities (e.g., the second semispherical cavities 41) based on spherical diameters, in this example, of 9.0 millimeters. The actual steps of forming the semispherical cavities using the first embodiment of the cutting instrument of the present invention after the joint 23 is exposed, etc., is clearly illustrated in FIGS. 4–7 with respect to the first and second cutting instruments 35, 39. Thus, to form the first semispherical cavities 37, the cutting instrument head 43 of the first cutting instrument 35 is merely held sidewise relative to the joint 23 as illustrated in FIG. 4, and then slid between the trapezium 19 and thumb metacarpal 21 and then rotated as somewhat diagrammatically illustrated in FIG. 5, thereby forming the matched pair of partial hemispherical impressions or semispherical cavities 37. The cutting instrument head 43 is then removed from the joint 23, and the above process is repeated with the cutting instrument head 61 of the second cutting instrument 39 (using the previously formed cavities 37 as guides, if desired) to form the matched pair of partial hemispherical impressions or semispherical cavities 41 based on spherical diameters, in this example, of 9.0 millimeters.

A second embodiment of the cutting instrument of the present invention is shown in FIGS. 8 and 18–21, and is especially designed to oscillate rather than fully rotate. This second embodiment also preferably includes a series or set of similar cutting instruments having incrementally larger cutting instrument heads for forming incrementally larger semispherical cavities. However, with this second embodiment of the cutting instrument, there is no incremental cutting of the semispherical cavities (i.e., the second embodiment of the cutting instrument is not intended to be used to enlarged previously cut or formed semispherical cavities). Rather, the joint gap (i.e., the width of the gap between the proximal surface 25 of the thumb metacarpal 21 and the distal surface 27 of the trapezium 19) is assessed with a sizer (i.e., with a feeler gauge 29) and then a single specific cutting instrument is selected based on the assessed size of the joint gap.

Figure 19:
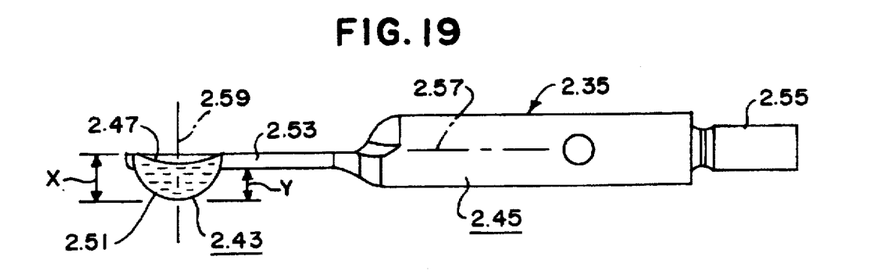
FIG. 19 is a front elevational view of the cutting instrument of FIG. 18.
Figure 20:
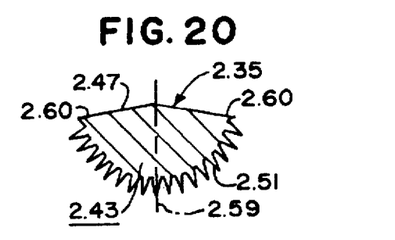
FIG. 20 is a sectional view substantially as taken on line 20—20 of FIG. 18, with portions omitted for clarity.
Figure 21:
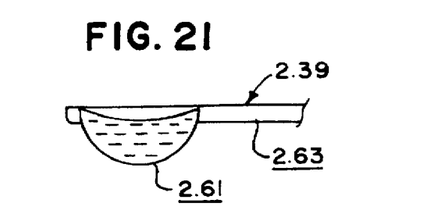
FIG. 21 is a front elevational view of a portion of a cutting instrument similar to FIG. 19 but showing ant incrementally larger cutting instrument of the instrumentation of the present invention.

This second embodiment preferably includes a cutting instrument 2.35 as shown in FIGS. 8 and 18–20 (hereinafter referred to as the "first" cutting instrument 2.35) for cutting semispherical cavities 37 in the proximal surface 25 of the thumb metacarpal 21 and the distal surface 27 of the trapezium 19, and a larger cutting instrument 2.39 as shown in FIG. 21 (hereinafter referred to as the "second" cutting instrument 2.39) for cutting larger semispherical cavities 41 in the proximal surface 25 of the thumb metacarpal 21 and the distal surface 27 of the trapezium 19. As hereinabove noted, the plurality of cutting instruments 2.35, 2.39, etc., of this second embodiment are not used incrementally, one after the other, to enlarge previously formed cavities. Rather, only one of the plurality of cutting instruments 2.35, 2.39, etc., is used to form cavities based on the measured or assessed joint gap or distance between the proximal surface 25 of the thumb metacarpal 21 and the distal surface 27 of the trapezium 19.

Figure 8:
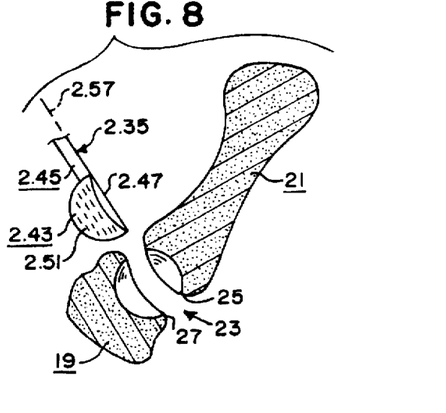
FIG. 8 is a somewhat diagrammatic, sectional view of the first metacarpal and the trapezium of a left hand, similar to FIG. 4 but showing an alternate embodiment of a cutting instrument being inserted into the gap between the proximal surface of the first metacarpal and the distal surface of the trapezium to cut semispherical cavities (e.g., cavities that are each substantially equal to an outer ⅓ of a sphere) in the proximal surface of the first metacarpal and in the distal surface of the trapezium.

The first cutting instrument 2.35 includes, in general, a cutting instrument head 2.43 and an elongated shaft 2.45 attached to the cutting instrument head 2.43 for allowing the cutting instrument head 2.43 to be oscillated (i.e., to be rotated back and forth). The cutting instrument head 2.43 preferably has the shape of a hemisphere with a truncated side 2.47, and a semispherical cutting edge or face surface 2.51. The shaft 2.45 has a first end 2.53 attached or joined to the cutting instrument head 2.43 and a second end 2.55 adapted to be coupled to a typical oscillating drill, handpiece or the like as will now be apparent to those skilled in the art. The shaft 2.45 thus allows the cutting instrument head 2.43 to be rotated about a rotational axis 2.57 that is coextensive with the longitudinal axis of the shaft 2.45 and that is generally transverse to an axis or plane 2.59 extending through the center of the cutting instrument head 2.43 (i.e., though the central segment of the sphere) between the truncated side 2.47 and the face surface 2.51 thereof (see FIGS. 19 and 20). The opposite edges 2.60 of the truncated side 2.47 are preferably angled downward somewhat along the rotational axis 2.57 as shown in FIG. 20 to provide relief clearances as the cutting instrument head 2.43 oscillates and so that, during operation, the effective arc of the cutting instrument head 2.43 does not strike the opposing bone surface. The thickness of the cutting instrument head 2.43 (i.e., the distance between the apex of the side 2.47 and the apex of the face surface 2.51 as indicated by the dimension "X" in FIG. 19) is preferably only slightly larger than the width of the gap between the proximal surface 25 of the thumb metacarpal 21 and the distal surface 27 of the trapezium 19 to allow the cutting instrument head 2.43 to easy slide, using light retraction, between the proximal surface 25 of the thumb metacarpal 21 and the distal surface 27 of the trapezium 19 as illustrated in FIG. 8. The dimension "X" is preferably ½ of the diameter of the cutting instrument head 2.43. The cross sectional size or width of at least the first end 2.53 of the shaft 2.45 adjacent the cutting instrument head 2.43 is preferably less than the width of the gap between the proximal surface 25 of the thumb metacarpal 21 and the distal surface 27 of the trapezium 19 to allow that portion of the shaft 2.45 to easy fit and rotate between the proximal surface 25 of the thumb metacarpal 21 and the distal surface 27 of the trapezium 19. The distance between the apex of the face surface 2.51 of the cutting instrument head 2.43 and the closest point of the first end 2.53 of the shaft 2.45 thereto as indicated by the dimension "Y" in FIG. 19 is preferably ⅓ of the diameter of the cutting instrument head 2.43.

The second cutting instrument 2.39 is preferably substantially similar of the first cutting instrument 2.35, including a cutting instrument head 2.61 and an elongated shaft 2.63 attached to the cutting instrument head 2.61 for allowing the cutting instrument head 2.61 to be rotated. However, the cutting instrument head 2.61 of the second cutting instrument 2.39 preferably has the shape of a hemisphere that is 0.5 millimeters in diameter larger than that of the cutting instrument head 2.43 of the first cutting instrument 2.35. As hereinabove noted, the first and second cutting instruments 2.35, 2.39 are not used incrementally, one after the other, to enlarge previously formed cavities. Rather, a selected one of the plurality of cutting instruments 2.35, 2.39, etc., is used to form a matched pair of semispherical cavities based on the measured or assessed joint gap or distance between the proximal surface 25 of the thumb metacarpal 21 and the distal surface 27 of the trapezium 19.

The size of the matched pair of partial hemispherical impressions or semispherical cavities formed with the second embodiment of cutting instruments is also preferably based on a spherical diameter equal to three times the width of the measured gap between the proximal surface 25 of the thumb metacarpal 21 and in the distal surface 27 of the trapezium 19. To form the matched pair of partial hemispherical impressions or semispherical cavities having a desired size based on the measured distance or gap between the proximal surface 25 of the thumb metacarpal 21 and in the distal surface 27 of the trapezium 19 in the proximal surface 25 of the thumb metacarpal 21 and in the distal surface 27 of the trapezium 19, using the second embodiment of the cutting instrument of the present invention, the measured distance or gap provides the size of the "only" cutting instrument to use. Thus, for example, if the measured distance or gap is 3.0 millimeters, the "only" cutting instrument used will be the first cutting instrument 2.35 which, as hereinabove described, is sized to cut or form semispherical cavities based on a spherical diameter of 9.0 millimeters. The actual steps of forming the semispherical cavities using the first cutting instrument 2.35 after the joint 23 is exposed, etc., includes applying traction to the joint 23 to further separate the trapezium 19 and thumb metacarpal 21 until the distance or gap between the proximal surface 25 of the thumb metacarpal 21 and the distal surface 27 of the trapezium 19 is sufficient to allow the cutting instrument head 2.41 of the first cutting instrument 2.35 to be inserted between the trapezium 19 and thumb metacarpal 21. Next, using one of the pilot holes 33 as a guide if desired, the face surface 2.51 of the cutting instrument head 2.41 is pressed against, for example, the proximal surface 25 of the thumb metacarpal 21 (the face surface 2.51 could be first pressed against the distal surface 27 of the trapezium 19 if desired) and oscillated thereagainst until the spherical cavity is fully formed or cut thereinto. Next, the cutting instrument head 2.41 is rotated 180° so that the face surface 2.51 of the cutting instrument head 2.41 can be similarly pressed against the distal surface 27 of the trapezium 19 and oscillated thereagainst until the spherical cavity is fully formed or cut thereinto.

Regardless of the group of cutting instruments used to form the matched pair of partial hemispherical impressions or semispherical cavities in the thumb metacarpal 21 and the trapezium 19, after being formed the matched pair of partial hemispherical impressions or semispherical cavities are then irrigated and debris removed.

At least one sizer, or trial instrument, and preferably a group or series of trial instruments having a graduated sequence of sizes, are provided to assess the required implant size, etc. The group of trial instruments, or sizers, preferably includes at least a sizer or trial instrument 65 as shown in FIGS. 9, 10 and 22–24 (hereinafter referred to as the "first" trial instrument 65), and a sizer or trial instrument 67 as shown in FIG. 25 (hereinafter referred to as the "second" trial instrument 67). In use, only one size trial instrument is used after the spherical cavities are prepared to ensure that the spherical cavities are prepared adequately and that joint motion will be good (e.g., the one trial instrument 67 selected is preferably based on a spherical diameter equal to three times the width of the measured gap between the proximal surface 25 of the thumb metacarpal 21 and in the distal surface 27 of the trapezium 19 or on a spherical diameter equal to the diameter of the cutting instrument head used to cut or form the semispherical cavities being assessed.

Figure 9:
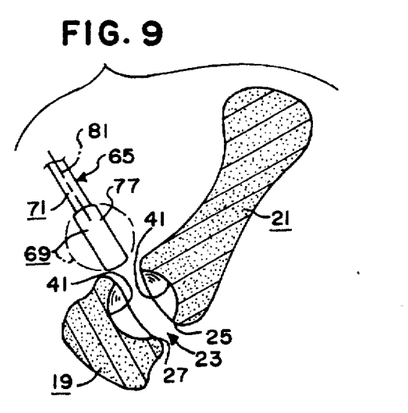
FIG. 9 is a somewhat diagrammatic, sectional view of the first metacarpal and the trapezium of a left hand, similar to FIG. 6 but showing a trial instrument, or sizer, being inserted into the gap between the proximal surface of the first metacarpal and the distal surface of the trapezium to assess the required spherical prosthesis size for implanting in the semispherical cavities in the proximal surface of the first metacarpal and the distal surface of the trapezium.
Figure 22:
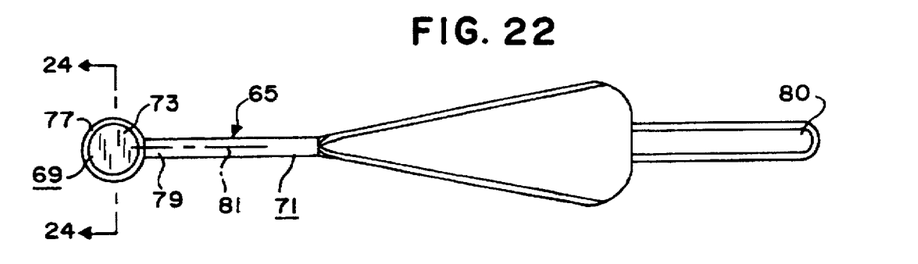
FIG. 22 is a top plan view of a trial instrument of the instrumentation of the present invention, the bottom plan being substantially similar thereof.
Figure 23:
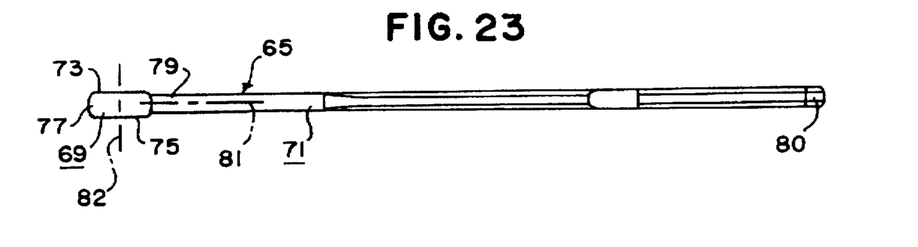
FIG. 23 is a front elevational view of the trial instrument of FIG. 22, the rear elevation being substantially similar thereof.
Figure 24:
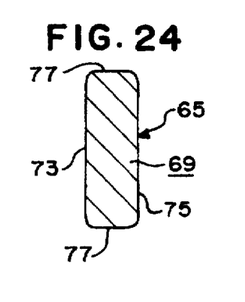
FIG. 24 is a sectional view substantially as taken on line 24—24 of FIG. 22, on a somewhat enlarged scale.
Figure 25:
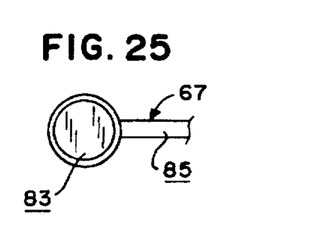
FIG. 25 is a top plan view of a portion of an incrementally larger trial instrument of the instrumentation of the present invention.

The first trial instrument 65 is shown in detail in FIGS. 22–24 and includes, in general, a trial instrument head 69 and an elongated shaft 71 attached to the trial instrument head 69 for allowing the trial instrument head 69 to be easily manipulated by a surgeon or the like. The trial instrument head 69 preferably has the shape of a central segment of sphere with a first truncated end 73, a second truncated end 75, and a semispherical face surface 77 extending between the first and second truncated ends 73, 75. The thickness of the trial instrument head 69 (i.e., the distance between the first and second truncated ends 73, 75 preferably measures approximately ¼ the spherical diameter of the trial instrument head 69. The shaft 71 has a first end 79 attached or joined to the trial instrument head 69 and a second end 80, preferably with a handgrip portion or the like located therebetween as clearly shown in FIGS. 22 and 23 for allowing a surgeon or the like to easily and comfortably grip and manipulate the first trial instrument 65 as will now be apparent to those skilled in the art. The shaft 71 thus allows the trial instrument head 69 to be rotated about a rotational axis 81 that is coextensive with the longitudinal axis of the shaft 71 and that is generally transverse to an axis or plane 82 extending through the center of the trial instrument head 69 (i.e. though the central segment of the sphere) between (and preferably perpendicular to the planar face of) the truncated ends 73, 75 thereof (see FIGS. 22 and 23). While the specific size of the trial instrument head 69 may vary for use with different size semispherical cavities as will now be apparent to those skilled, for purposes of this disclosure and based on the examples given hereinabove relative to the first and second cutting instruments 35, 39, the trial instrument head 69 will be considered to be sized based on a spherical diameter of, for example, 9.0 millimeters. The thickness of the trial instrument head 69 (i.e., the distance between the first end 73 and the second end 75) is preferably no greater than, and may be less than, the width of the gap between the proximal surface 25 of the thumb metacarpal 21 and the distal surface 27 of the trapezium 19 to allow the trial instrument head 69 to easy slide between the proximal surface 25 of the thumb metacarpal 21 and the distal surface 27 of the trapezium 19 when turned or held sideways relative to the joint 23 as illustrated in FIG. 9. The cross sectional size or width of at least the first end 79 of the shaft 71 adjacent the trial instrument head 69 is preferably less than the width of the gap between the proximal surface 25 of the thumb metacarpal 21 and the distal surface 27 of the trapezium 19 to allow that portion of the shaft 71 to easily fit and rotate between the proximal surface 25 of the thumb metacarpal 21 and the distal surface 27 of the trapezium 19.

The second trial instrument 67 shown in FIG. 25 is preferably substantially similar of the first trial instrument 65, including a trial instrument head 83 and an elongated shaft 85 attached to the trial instrument head 83 for allowing the trial instrument head 83 to be easily manipulated by a surgeon or the like. However, the trial instrument head 83 of the second trial instrument 67 preferably has the shape of a central segment of a sphere that is 1.0 millimeters in diameter larger than that of the trial instrument head 69 of the first trial instrument 65. Thus, based on the example given hereinabove relative to the trial instrument head 69, for purposes of this disclosure, the trial instrument head 83 will be considered to be sized based on a spherical diameter of, for example, 10 millimeters.

The actual number of trial instruments included in the group thereof may vary depending on the patient, etc. For example, a full group of trial instruments may include a series of four different size trial instruments starting with a trial instrument head based on a spherical diameter of 8.0 millimeters and increasing incrementally in size to include trial instruments with trial instrument heads based on discrete spherical diameters of 9.0 millimeters, 10.0 millimeters, and 11.0 millimeters, etc.

Figure 10:
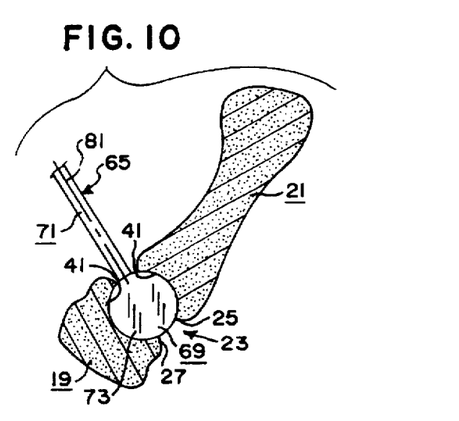
FIG. 10 is a somewhat diagrammatic, sectional view of the first metacarpal and the trapezium of a left hand, similar to FIG. 9 but showing the trial instrument thereof fully inserted between the proximal surface of the first metacarpal and the distal surface of the trapezium, and rotated 90° relative to the position shown in FIG. 9.

In any event, after the matched pair of partial hemispherical impressions or semispherical cavities in the thumb metacarpal 21 and the trapezium 19 have been irrigated and debris removed, a desired size trial instrument is selected and inserted or placed in the joint, etc. The actual trial instrument selected is preferably based on a spherical diameter equal to three times the width of the measured gap between the proximal surface 25 of the thumb metacarpal 21 and in the distal surface 27 of the trapezium 19. Using the examples heretofore given, with the "final" semispherical cavities 41 cut or formed by the second cutting instrument 39 based on a spherical diameter of 9.0 millimeters, the trial instrument head 69 of the first trial instrument 65 is inserted sideways between the prepared proximal surface 25 of thumb metacarpal 21 and the distal surface 27 of the trapezium 19 as somewhat diagrammatically illustrated in FIGS. 9 and 10. After being thus slid sideways between the opposing ends of the bones, the trial instrument head 69 is rotated 90° or so until the trial instrument head 69 extends substantially from the vertex of the semispherical cavity 41 in the proximal surface 25 of the thumb metacarpal 21 to the vertex of the semispherical cavity 41 in the distal surface 27 of the trapezium 19 as illustrated in FIG. 10, so that the semispherical face surface 77 of the trial instrument head 69 extends into and engages at least a portion of the walls of the semispherical cavities 41, i.e., with the section of the sphere held in line with the longitudinal axis of the thumb metacarpal 21. Thumb stability can then be tested by attempting to withdraw the trial instrument head 69 from the carpometacarpal joint 23. With the trial instrument 65 oriented in a radial ulnar direction, the thumb adduction and extension are measured. With the trial instrument 65 held in a palmar dorsal orientation, thumb extension and palmar abduction are measured. Restriction of motion from excessive tightness of the trial instrument head 69 indicates that one or both of the semispherical cavities 41 should be deepened or enlarged by removing the trial instrument head 69 from the joint and enlarging one or both semispherical cavities 41 using the process described hereinabove, and trial reduction of the joint is then again performed using a larger trial instrument until the surgeon is satisfied with the motion and stability of the joint, etc.

Once the surgeon is satisfied, the trial instrument 65 is removed and the wound is re-irrigated and debris removed. After appropriate preparation of the bone, the joint is ready for actual prosthesis implantation.

Figure 26:
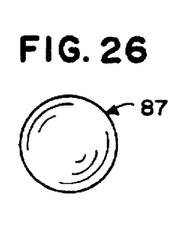
FIG. 26 is a perspective view of a spherical prosthesis of the present invention.
Figure 27:
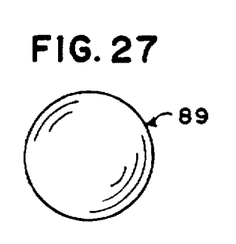
FIG. 27 is a perspective view of an incrementally larger spherical prosthesis of the present invention.

A group of spherical prostheses, having a graduated sequence of sizes, are provided for implanting into the semispherical cavities 41. The group of spherical prostheses preferably includes at least a spherical prosthesis 87 as shown in FIGS. 11, 12 and 26 (hereinafter referred to as the "first" spherical prosthesis 87), and a spherical prosthesis 89 as shown in FIG. 27 (hereinafter referred to as the "second" spherical prosthesis 89).

The actual number of spherical prostheses included in the group thereof may vary depending on the patient, etc. For example, a full group of spherical prostheses may include a series of different size spherical prostheses starting with a spherical prosthesis having a spherical diameter of 9.0 millimeters and increasing in size by 1.0 millimeters each step to a spherical prosthesis having a spherical diameter of 12.0 millimeters or more. Thus, for example, the first spherical prosthesis 87 may have a spherical diameter of 9.0 millimeters and the second spherical prosthesis 89 may have a spherical diameter of 10.0 millimeters. In any event, one of the group of spherical prostheses is selected for implanting into the "final" semispherical cavities, e.g., the semispherical cavities 41 shown in FIGS. 11 and 12. The specific spherical prosthesis selected is also preferably based on the measured gap between the proximal surface 25 of the thumb metacarpal 21 and the distal surface 27 of the trapezium 19. Thus, for purposes of this disclosure and based on the examples given hereinabove the specific spherical prosthesis selected will be considered to be based on a spherical diameter of 9.0 millimeters.

Figure 11:
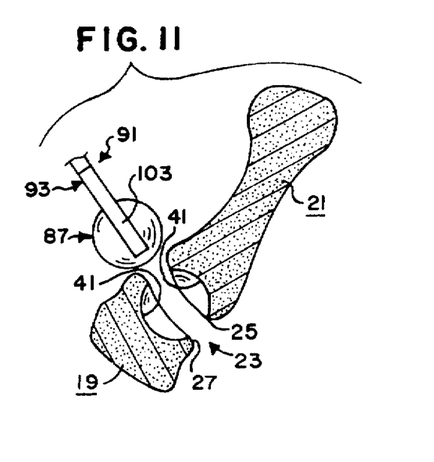
FIG. 11 is a somewhat diagrammatic, sectional view of the first metacarpal and the trapezium of a left hand, similar to FIG. 9 but diagrammatically showing an inserter being used to insert a spherical prosthesis between the proximal surface of the first metacarpal and the distal surface of the trapezium.
Figure 12:
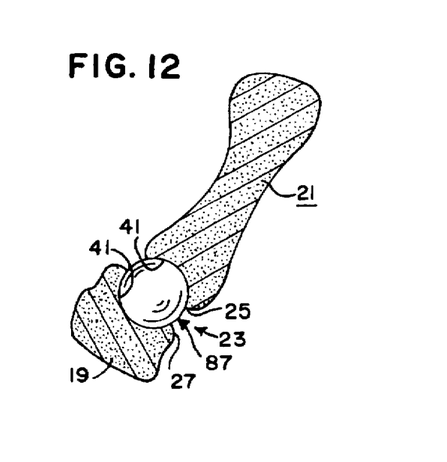
Figure 13:
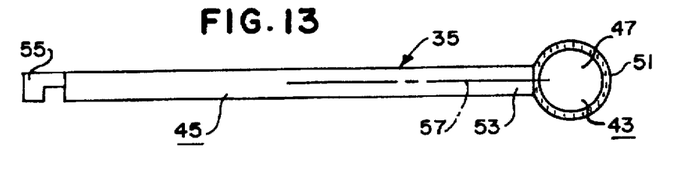
FIG. 13 is a top plan view of a cutting instrument of the present invention, the bottom plan view being substantially similar thereof.
Figure 14:
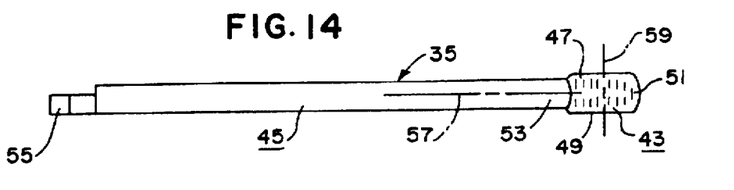
FIG. 14 is a front elevational view of the cutting instrument of FIG. 13.
Figure 15:
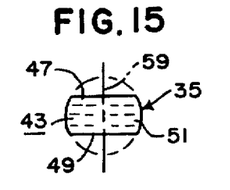
FIG. 15 is a right end elevational view of the cutting instrument of FIG. 13.
Figure 16:
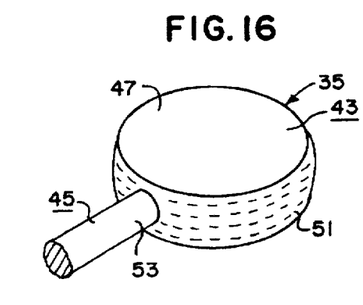
FIG. 16 is a perspective view of the cutting head of the cutting instrument of FIG. 13 as taken from the top, left on a somewhat enlarged scale.

For illustrative purposes, FIGS. 11 and 12 shows the first spherical prosthesis 87 being inserted between the prepared proximal surface 25 of thumb metacarpal 21 and the distal surface 27 of the trapezium 19 and implanted into the semispherical cavities 41.

Figure 28:
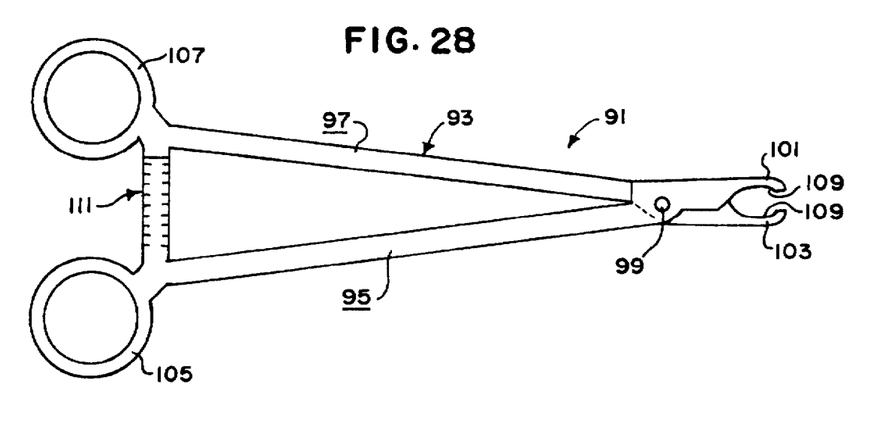
FIG. 28 is a front elevational view of an inserter of the instrumentation of the present invention.
Figure 29:
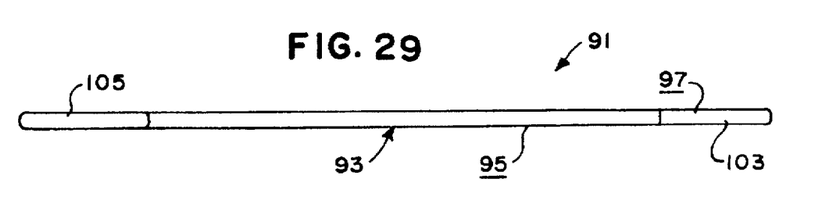
FIG. 29 is a side elevational view of the inserter of FIG. 28.

An implant inserter 91 (see FIGS. 11, 28 and 29) is provided and utilized to secure and guide the selected spherical prosthesis for implantation. The inserter 91 may consist of forceps 93 having a first elongated limb 95 and a second elongated limb 97 pivotally jointed together between the opposite ends thereof by a pivot 99, thus forming opposing first and second jaws 101, 103 and opposing first and second handles 105, 107. Each jaw 101, 103 may have a curved or somewhat semispherical grip surface 109 for allowing the forceps 93 to securely grip a selected one of the group of spherical prostheses. The forceps 93 preferably include lock means 111 for allowing the jaws 101, 103 to be locked onto the selected spherical prosthesis as will now be apparent to those skilled in the art. The width or thickness of at least the distal ends of the first and second jaws 101, 103 are preferably less than the width of the gap between the proximal surface 25 of the thumb metacarpal 21 and the distal surface 27 of the trapezium 19 to allow that portion of the first and second jaws 101, 103 to easily fit between the proximal surface 25 of the thumb metacarpal 21 and the distal surface 27 of the trapezium 19 as illustrated in FIG. 11.

Once the selected spherical prosthesis, e.g., the spherical prosthesis 87, is locked to inserter 91, the soft tissues are retracted and steady, firm pressure is applied to the inserter 91 so that after appropriate soft tissue relaxation, the spherical prosthesis 87 will slip over the bony margins of the trapezium 19 and metacarpal 21, and clunk or audibly slip into position as shown in FIGS. 11 and 12. Stability of the spherical prosthesis 87 is tested by attempting to withdraw the spherical prosthesis 87 with the inserter 91. The inserter 91 can then be removed from the spherical prosthesis 87, etc.

Once appropriate stability has been achieved, the trapezium based capsular flap is sutured to the metacarpal abductor pollicis longus insertion. The would is re-irrigated and skin closed with appropriate suture material and dressed with a non-adherent gauze prior to application of a thumb spica splint with the thumb in 30°–40° of palmar abduction and 20°–30° of radial abduction.

The various instruments (e.g., the cutting instruments, trial instruments, etc.) may be constructed in various manners and out of various materials as will now be apparent to those skilled in the art. Thus, for example, the various instruments may be machined or otherwise constructed out of stainless steel or the like, in various sizes, etc. The cutting or face surfaces of the cutting instrument heads of the various cutting instruments may have teeth cut or formed therein or may have an abrasive coating applied thereto, etc., in any manner now apparent to those skilled in the art for removing bone when rotated or oscillated.

The spherical prostheses may be constructed in various manners and out of various materials as will now be apparent to those skilled in the art. Thus, for example, each spherical prosthesis can be machined, molded or otherwise constructed as a one-piece, integral unit out of a medical grade, physiologically acceptable ceramic or metal, etc., such as zirconium, titanium or the like, in various sizes to fit a range of typical patients, or may be custom-designed for a specific patient based on data provided by a surgeon after physical and radiography examination of the specific patient, etc.

Although the present invention has been described and illustrated with respect to preferred embodiments and a preferred use therefor, it is not to be so limited since modifications and changes can be made therein which are within the full intended scope of the invention.

We claim:

1. A method of implanting a spherical prosthesis in a joint between a first bone having a proximal surface and a second bone having a distal surface; the method comprising the steps of:

(a) exposing the joint between the first bone and the second bone;

(b) measuring the distance between the proximal surface of the first bone and the distal surface of the second bone;

(c) forming a semispherical cavity in the proximal surface of the first bone to a depth substantially equal to the distance between the proximal surface of the first bone and the distal surface of the second bone;

(d) forming a semispherical cavity in the distal surface of the second bone to a depth substantially equal to the distance between the proximal surface of the first bone and the distal surface of the second bone;

(d) providing the spherical prosthesis having a diameter substantially three times the distance between the proximal surface of the first bone and the distal surface of the second bone; and then (e) inserting the spherical prosthesis into the semispherical cavities formed in the proximal surface of the first bone and in the distal surface of the second bone.

2. A method of implanting a spherical prosthesis in a joint between a first bone having a proximal surface and a second bone having a distal surface, the proximal surface of the first bone being spaced from the distal surface of the second bone a certain distance; the method comprising the steps of:

(a) exposing the joint between the first bone and the second bone;

(b) forming a semispherical cavity in the proximal surface of the first bone;

(c) forming a semispherical cavity in the distal surface of the second bone;

(d) providing a trial instrument including a trial instrument head having the shape of a central segment of a sphere with a first end, a second end, and a semispherical face surface extending between the first and second ends and with at least one of the ends of the trial instrument head truncated;

(e) inserting the trial instrument head into the joint between the proximal surface of the first bone and in the distal surface of the second bone; then (f) rotating the trial instrument head until the trial instrument head extends substantially from the vertex of the semispherical cavity in the proximal surface of the first bone to the vertex of the semispherical cavity in the distal surface of the second bone; then (g) moving the first and second bones relative to one another to test the fit of the trial instrument head within the semispherical cavities in the proximal surface of the first bone and in the distal surface of the second bone; and then (h) inserting the spherical prosthesis into the semispherical cavities formed in the proximal surface of the first bone and in the distal surface of the second bone.

3. The method of claim 2 in which is included the step of measuring the distance between the proximal surface of the first bone and the distal surface of the second bone before the steps of forming semispherical cavities in the proximal surface of the first bone and the distal surface of the second bone; in which the semispherical cavity formed in the proximal surface of the first bone is formed to a depth substantially equal to the distance between the proximal surface of the first bone and the distal surface of the second bone; and in which the semispherical cavity formed in the distal surface of the second bone is formed to a depth substantially equal to the distance between the proximal surface of the first bone and the distal surface of the second bone.

4. A method of implanting a spherical prosthesis in a joint between a first bone having a proximal surface and a second bone having a distal surface; the method comprising the steps of:

(a) exposing the joint between the first bone and the second bone;

(b) providing a cutting instrument including a cutting instrument head having the shape of a central segment of a sphere with a first end, a second end, and a semispherical cutting surface extending between the first and second ends and with at least one of the ends of the cutting instrument head truncated;

(c) inserting the cutting instrument head into the joint between the proximal surface of the first bone and the distal surface of the second bone; then (d) rotating the cutting instrument head to simultaneously cut semispherical cavities in the proximal surface of the first bone and in the distal surface of the second bone; and then (e) inserting the spherical prosthesis into the semispherical cavities formed in the proximal surface of the first bone and in the distal surface of the second bone.

5. A method of preparing a joint to receive a spherical prosthesis in a joint between a first bone having a proximal surface and a second bone having a distal surface; the method comprising the steps of:

(a) exposing the joint between the first bone and the second bone;

(b) providing a cutting instrument including a cutting instrument head having the shape of a semisphere with a truncated side and a semispherical cutting edge;

(c) applying traction to the first and second bones to further separate the proximal and distal surfaces thereof; then (d) inserting the cutting instrument head into the joint between the proximal surface of the first bone and the distal surface of the second bone; then (e) pressing the cutting instrument head against the proximal surface of the first bone; then (f) oscillating the cutting instrument head to form a semispherical cavity in the proximal surface of the first bone; then (g) rotating the cutting instrument head 180°; then (h) pressing the cutting instrument head against the distal surface of the second bone; and then (i) oscillating the cutting instrument head to form a semispherical cavity in the distal surface of the second bone.

* * * * *